United States Patent
Graumann

(10) Patent No.: US 7,742,569 B2
(45) Date of Patent: Jun. 22, 2010

(54) X-RAY SYSTEM AND METHOD FOR IMAGE COMPOSITION

(75) Inventor: Rainer Graumann, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 105 days.

(21) Appl. No.: 12/178,017

(22) Filed: Jul. 23, 2008

(65) Prior Publication Data

US 2009/0028291 A1    Jan. 29, 2009

(30) Foreign Application Priority Data

Jul. 23, 2007    (DE) .................. 10 2007 034 218

(51) Int. Cl.
*H05G 1/60* (2006.01)
(52) U.S. Cl. .................. 378/98.12; 378/206; 378/62
(58) Field of Classification Search ............. 378/98.12, 378/62, 205, 206, 163
See application file for complete search history.

(56) References Cited

U.S. PATENT DOCUMENTS

| 6,473,489 | B2  | 10/2002 | Bani-Hashemi et al. |
| 6,484,049 | B1* | 11/2002 | Seeley et al. ................ 600/426 |
| 6,714,622 | B2  | 3/2004  | Horbaschek |
| 7,302,030 | B2  | 11/2007 | Bruder et al. |
| 2002/0012420 | A1* | 1/2002 | Bani-Hashemi et al. ....... 378/63 |
| 2004/0254456 | A1  | 12/2004 | Ritter |

FOREIGN PATENT DOCUMENTS

DE    10 2005 062 582    7/2007

* cited by examiner

*Primary Examiner*—Hoon Song
(74) *Attorney, Agent, or Firm*—Schiff Hardin LLP

(57) ABSTRACT

In an x-ray system and a method for image composition, congruent optical images and x-ray images of subjects provided with markers are generated. A transformation matrix/imaging matrix is formed and applied to the congruent x-ray images based on the detected identical markers in optical images. The transformation matrix is used to compose an aggregate image from the x-ray images.

12 Claims, 2 Drawing Sheets

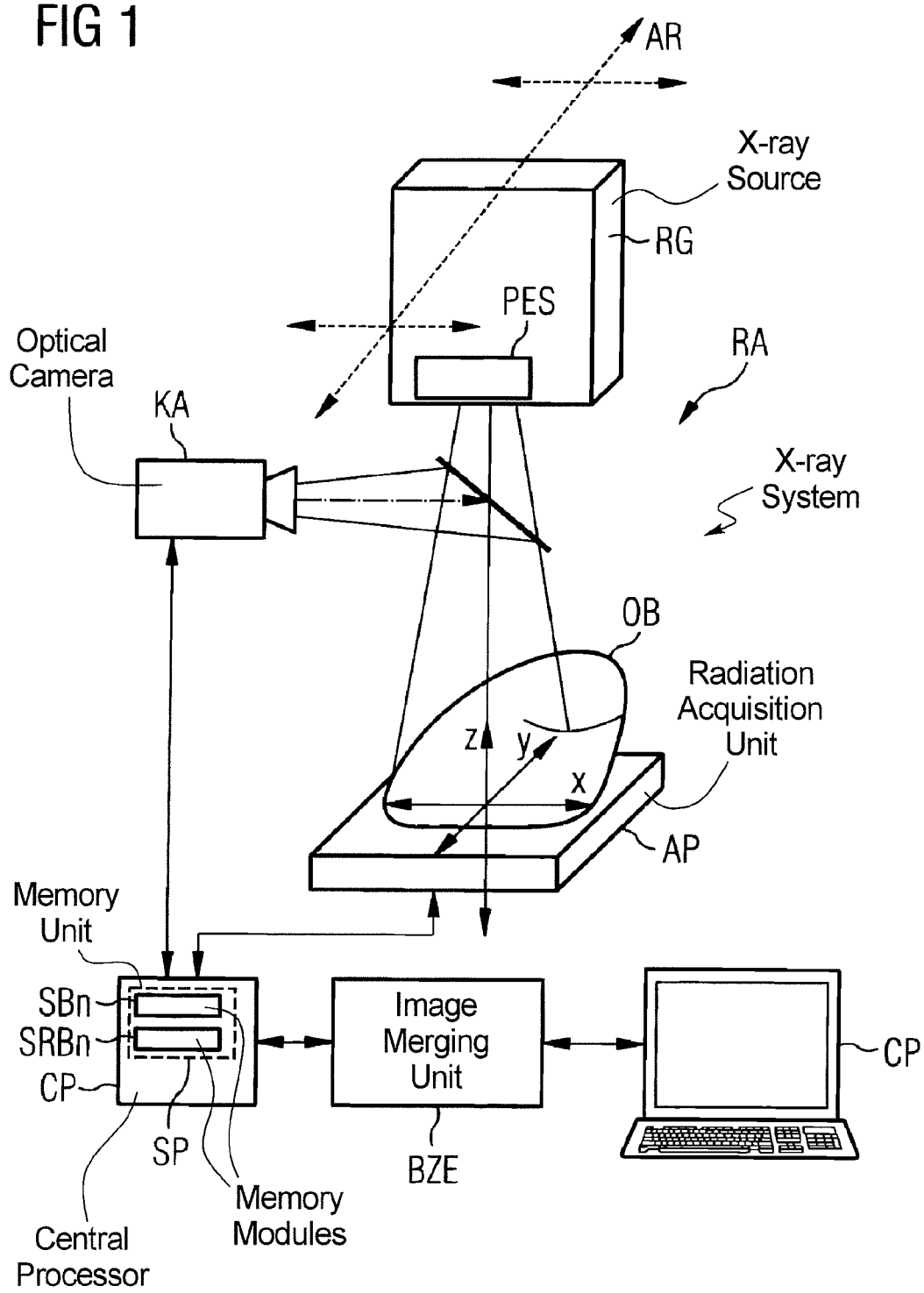

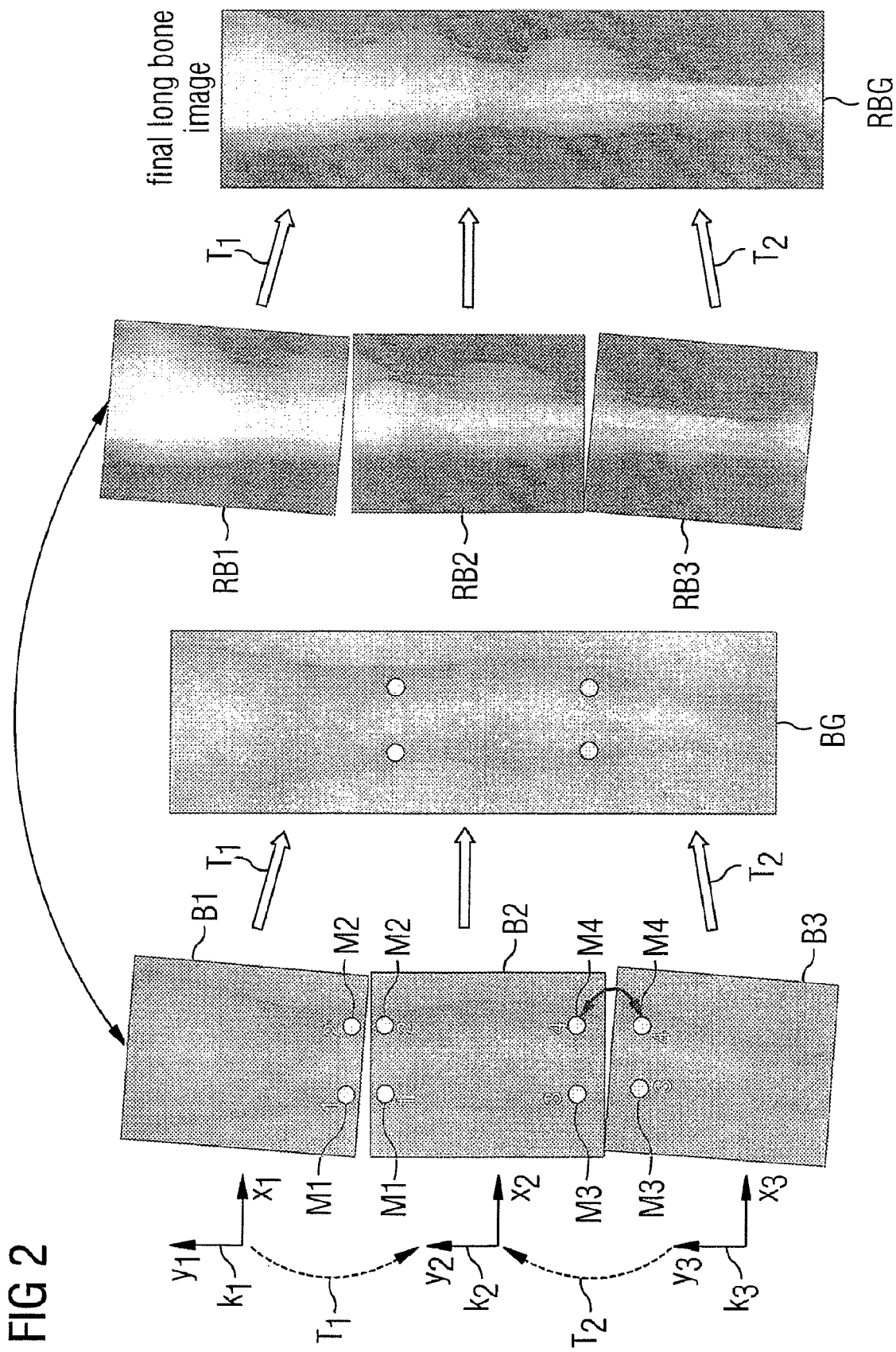

X-RAY SYSTEM AND METHOD FOR IMAGE COMPOSITION

BACKGROUND OF THE INVENTION

1. Field of the Invention

The present invention concerns an x-ray system and a method for a composition of an image composed of at least two individual images.

2. Description of the Prior Art

X-ray exposures are produced to support medical diagnosis or therapy. Tissue, vascular and in particular bone structures of body parts can be considered in detail, section by section, with the x-ray images. Although the anatomy of interest can often be completely shown in an individual x-ray image, it is also often desired to image larger structures that do not fit a single x-ray exposure (such as, for example, the curve of the spinal column, a leg or an arm) for therapeutic or operative measures. For this purpose, a number of x-ray projection exposures of the subject to be considered is to be produced with a predeterminable resolution. The individual x-ray exposures must then be assembled so that a geometrically exact aggregate image of the x-rayed body regions results.

SUMMARY OF THE INVENTION

An object of the present invention is to provide a device and an associated method to generate an aggregate image.

The above object is achieved in accordance with the present invention by an x-ray system and a method for image composition, wherein optical images of a subject and x-ray images of a subject, that are congruent with the optical images, are generated, with the subject being provided with markers during the image acquisition. The markers are detectable in both sets of images. A transformation matrix/imaging matrix is formed and is applied to the respective x-ray images based on the detected identical markers in the optical images that are respectively congruent thereto. The transformation matrix/imaging matrix is used to compose an aggregate image from the x-ray images.

With the device and the associated method, congruent images of simultaneously acquired first and second individual image series can be generated from a subject provided with markers. An image composition unit is designed such that the positions of associated markers can be detected and generated in first and second images of the first individual image series. The image content of a first image of the second individual image series is converted into the coordinate system of a second image using the imaging parameters of an imaging matrix.

The invention has the advantage that only the x-ray images actually required for diagnosis must be acquired, which results in the further advantage that the x-ray exposure for the subject is reduced. Spatially intermediate x-ray exposures that are acquired only for the purpose of the image merging are not required.

In addition to the advantage that the first and second individual image series have a fixed geometrical relation relative to one another, the invention entails the further advantage that these can also be associated with one another given different acquisition geometries.

The invention also has the advantage that a transition-free aggregate image made up of a plurality of individual images can be generated with a small expenditure of computing time and computing capacity to be provided.

The invention also has the advantage that geometrically exact relationships between non-overlapping x-ray exposures can also be achieved.

The invention also achieves the advantage that no elaborate and error-prone, image-based correlation algorithms with small overlap regions need to be used for image merging.

The invention also provides the advantage that no invasive marker points must be used.

The invention has the further advantage that an enlargement of the visible image region can be achieved via a simple image zoom function.

BRIEF DESCRIPTION OF THE DRAWINGS

FIG. 1 schematically illustrates basic components of an embodiment of an x-ray system constructed and operating in accordance with the present invention.

FIG. 2 illustrates a composition of individual images in accordance with the present invention.

DESCRIPTION OF THE PREFERRED EMBODIMENTS

An x-ray system RA has an x-ray source RG and a radiographic acquisition unit AP as well as an optical image acquisition unit KA is shown in FIG. 1. First and second individual image series acquired by the x-ray system RA and the image acquisition unit KA are cached in memory units SB1, . . . , SBn, SRB1, . . . , SRBn of a memory module SP of a central processor CP. The images of the first individual image series are individual optical images, and the images of the second individual image series are individual x-ray images. Each of the x-ray system RA and the optical image acquisition unit KA, which may be a photographic camera or a video camera, is controlled by a processor such that congruent first and second individual image series can be generated with regard to a subject OB to be examined. X-ray exposures of medically uninteresting regions thus can be omitted. Only optical images in the first individual image series are generated in this region. The first individual exposure Bn (an optical image or video exposure) and the second individual image series RB (an x-ray exposure) are cached in the memory unit SP. The respective first and second individual exposures Bn, RBn are converted by an image processor into first and second aggregate images BG, RBG in an image merging unit BZE by means of transformation matrices.

FIG. 2 schematically shows the composition of first and second images Bn, RBn of the first and second individual image series B, RB to form first and second aggregate images BG, RBG. A number of x-ray-permeable marker points M1, M2, M3, M4 are applied on the subject OB to be examined before individual image exposures of the appertaining subject are acquired. These marker points can be applied on the subject or a (sterile) patient covering with using a marker pen that, for example, dispenses a soluble ink that contrasts with skin color.

If a subject OB is larger than a typically-employed acquisition unit AP, a number of x-ray exposures RB1, RB2, . . . with associated optical images B1, B2, . . . are thus required.

In order to produce a number of individual exposures, the x-ray system RA and the camera system KA connected therewith are moved along a subject OB on guide elements, for example a rail AR. A first individual image series and a second individual image series (i.e. optical images Bn and x-ray images RBn) are thereby generated. These individual image series render the subject OB in parts. While the subject OB is being completely covered by overlapping optical image exposures Bn, corresponding x-ray exposures in medically irrelevant regions can be foregone. The sequence of optical image exposures Bn of the first individual image series B is thereby designed such that a minimum number of associated marker points is imaged as well in successive optical image/ video exposures.

In the shown first individual image series B with the optical images B1, B2, B3, the markers M1, M2 are imaged in the first optical image B1. The second optical image B2 contains the marker points M1, M2, M3, M4; the third optical image B3 contains the marker points M3, M4. As explained above, x-ray images RB1, RB2 and RB3 can also be generated congruent with the optical images B1, B2 and B3 in a second individual image series. The respective individual x-ray images can exist in digital data. The x-ray images RB1, RB2, RB3 as well as the image data B1, B2, B3 are cached in a memory unit SP. The memories SB1, . . . , SBn are thereby provided for the image data and the memories SRB1, . . . , SRBn are provided for the x-ray images. The coordinates K1, K2, K3 of the image planes are likewise cached with regard to the individual image series B1, B2, B3. A first transformation T1 between a first coordinate system K1 (X1, Y1) of the first individual image B1 and a second coordinate system K2 (X2, Y2) of the second individual image B2 is respectively calculated in an intervening step. The displacement of marker points between the first image and second image in the x-direction and y-direction as well as a possible rotation in the image plane are respectively determined to calculate a first transformation matrix between the first and second images. After a determination of a displacement and/or rotation with regard to the same marker points, a transformation of image points of a first image into the first coordinate system K1 can be transferred into/onto a second image of the second coordinate system K2. The map of the first image then seamlessly carries over into the second image. Overlapping image elements are separated. A second transformation T2 is calculated between the coordinate systems K3 (X2,Y3) and K2 (X2,Y2) of the third and second individual image B3, B2. An aggregate optical image BG is generated from three individual optical images B1, B2, B3 with the use of the first and second transformation T1, T2. The respective transformations between the optical images can be applied to the x-ray images acquired in parallel with the optical images. In addition to an aggregate image BG generated from optical images B1, B2, an aggregate x-ray image RBG is generated from individual x-ray image RB1, RB2, RB3. For example, the congruent optical images and x-ray images B1, RB1; B2, RB2 and B3, RB3 are acquired in connection with a 2D Camera Augmented Mobile C-Arm (CAMC) device.

An exemplary embodiment that generates a spatially precise overlay of an x-ray projection image with a real-time video image proceeding from a Camera Augmented Mobile C-Arm (CAMC) device is described below with regard to the device and the associated method described above. The following steps are thereby implemented:

A: Application or attachment of x-ray-permeable optical markers M1, M2, . . . on the surface of a subject or patient OB. The number of the positions of the marker points is dependent on the size of a measurement window. Since only displacements in two directions $\Delta X$, $\Delta Y$ and/or a rotation ($\Delta \alpha$) can occur given the same subject-focus distance, only two corresponding points (4 known variables X1, Y1, X2, Y2) are respectively required for the calculation of the transformation of two images. The requirement is that the x-ray device RA does not tilt between two exposures. If the distance between the acquisition device and the patient varies slightly, a scaling quantity per projection could also be determined from the measurement values. If more than two corresponding points per image pair are provided, additional parameters (such as tilts) can be determined.

B: Congruent x-ray exposures and video exposures are acquired in parallel, corresponding to the size of the acquisition window. The video images are subsequently strung together using the marker positions identifiable in the images, as described above. Resulting from this are transformations T1, T2 from video image to video image that are then applied to the x-ray images for image composition since video image and x-ray image exhibit identical projections.

C: The x-ray images can be merged or converted by means of the transformation matrix. Individual images that exhibit no overlap (such as, for example, hip exposure, knee exposure and ankle exposure) can be used to determine the leg axes. Only the optical images of the intervening regions are additionally acquired, and transformation matrices are derived from these. This leads to a significant dose reduction.

D: The acquisition unit can be equipped with an adjustable zoom objective that allows it to show larger subject regions.

E: The image composition is possible in arbitrary directions. The marker points are either determined manually or automatically detected in the video images and associated with the positions. The automatic detection of the marker points occurs either via the use of correlation methods (given structures that are known and always remain the same) or via the segmentation of the structures with subsequent pattern recognition. A user direction for optimal positioning of marker points can be obtained in the software for easier implementation capability.

Although modifications and changes may be suggested by those skilled in the art, it is the intention of the inventors to embody within the patent warranted hereon all changes and modifications as reasonably and properly come within the scope of their contribution to the art.

I claim as my invention:

1. An x-ray system comprising:
 a radiographic image acquisition unit that acquires a plurality of radiographic images of a subject;
 an optical image acquisition unit that acquires a plurality of optical images of the examination subject that are respectively congruent to said x-ray images, said subject having markers applied thereto during acquisition of said radiographic images and during acquisition of said optical images, said markers being visible in each of said optical images and said radiographic images;
 an image processor that detects respective positions of said markers in each of said optical images and said radiographic images and that is configured to calculate a transformation matrix dependent on the respective positions of the markers in the respective optical images and the respective radiographic images; and
 said image processor being configured to compose an aggregate image of said x-ray images using said transformation matrix to convert an image content of a first of the radiographic images into a coordinate system of a second of the radiographic images to combine said first of said radiographic images with said second of said radiographic images with the same coordinate system in said aggregate image.

2. An x-ray system as claimed in claim 1 wherein said radiographic image acquisition unit and said optical image acquisition are configured to operate in synchronization to acquire said radiographic images and said optical images simultaneously and in geometrical congruence.

3. An x-ray system as claimed in claim 1 wherein said radiographic image acquisition unit and said optical image acquisition unit have a fixed geometrical relationship to each other, so that said radiographic images and said optical images also have said fixed geometrical relationship with each other.

4. An x-ray system as claimed in claim 1 comprising a memory, accessible by said image processor, in which said optical images and said radiographic images are stored during acquisition thereof.

5. An x-ray system as claimed in claim 1 wherein said image processor stores respective coordinate transformations between a coordinate system of the first of the radiographic images and the coordinate system of the second of the radiographic images.

6. An x-ray system as claimed in claim 1 wherein said image processor is configured to mask any overlapping regions between the respective radiographic images in said aggregate image.

7. An x-ray system as claimed in claim 1 wherein said image processor is configured to calculate a further transformation matrix from the respective positions of said markers, and to generate a second aggregate image from said radiographic images using said further transformation matrix.

8. A method for combining x-ray images comprising the steps of:

acquiring a plurality of radiographic images of a subject;

acquiring a plurality of optical images of the examination subject that are respectively congruent to said x-ray images, said subject having markers applied thereto during acquisition of said radiographic images and during acquisition of said optical images, said markers being visible in each of said optical images and said radiographic images;

automatically electronically detecting respective positions of said markers in each of said optical images and automatically electronically calculate a transformation matrix dependent on the respective positions of the markers in the respective optical images and the respective radiographic images; and automatically electronically composing an aggregate image of said x-ray images using said transformation matrix to convert an image content of a first of the radiographic images into a coordinate system of a second of the radiographic images to combine said first of said radiographic images with said second of said radiographic images with the same coordinate system in said aggregate image.

9. A method as claimed in claim 8 comprising acquiring said radiographic images and said optical images simultaneously and in geometrical congruence.

10. A method as claimed in claim 8 comprising acquiring said radiographic images and said optical images respectively with a radiographic image acquisition unit and an optical image acquisition unit have a fixed geometrical relationship to each other, so that said radiographic images and said optical images also have said fixed geometrical relationship with each other.

11. A method as claimed in claim 8 comprising electronically masking any overlapping regions between the respective radiographic images in said aggregate image.

12. A method as claimed in claim 8 comprising automatically electronically calculating a further transformation matrix from the respective positions of said markers, and generating a second aggregate image from said radiographic images using said further transformation matrix.

* * * * *